US011517605B2

(12) United States Patent
Cheng

(10) Patent No.: US 11,517,605 B2
(45) Date of Patent: Dec. 6, 2022

(54) MECHANISM BASED QUALITY CONTROL FOR BOTANICAL MEDICINE

(71) Applicant: YALE UNIVERSITY, New Haven, CT (US)

(72) Inventor: YungChi Cheng, Woodbridge, CT (US)

(73) Assignee: YALE UNIVERSITY, New Haven, CT (US)

(*) Notice: Subject to any disclaimer, the term of this patent is extended or adjusted under 35 U.S.C. 154(b) by 499 days.

(21) Appl. No.: 16/312,029

(22) PCT Filed: Jun. 21, 2017

(86) PCT No.: PCT/US2017/038421
§ 371 (c)(1),
(2) Date: Dec. 20, 2018

(87) PCT Pub. No.: WO2017/223131
PCT Pub. Date: Dec. 28, 2017

(65) Prior Publication Data
US 2019/0374593 A1 Dec. 12, 2019

Related U.S. Application Data

(60) Provisional application No. 62/353,313, filed on Jun. 22, 2016.

(51) Int. Cl.
*A61K 36/539* (2006.01)
*A61K 36/65* (2006.01)
*A61K 36/484* (2006.01)
*A61K 36/725* (2006.01)

(52) U.S. Cl.
CPC .......... *A61K 36/539* (2013.01); *A61K 36/484* (2013.01); *A61K 36/65* (2013.01); *A61K 36/725* (2013.01)

(58) Field of Classification Search
CPC ..... A61P 35/00; A61K 36/725; A61K 36/484; A61K 36/539; A61K 36/65; A61K 2300/00
See application file for complete search history.

(56) References Cited

U.S. PATENT DOCUMENTS

| | | | |
|---|---|---|---|
| 7,025,993 | B2 | 4/2006 | Cheng et al. |
| 7,534,455 | B2 | 5/2009 | Cheng et al. |
| 10,646,530 | B2 | 5/2020 | Liu et al. |
| 2003/0207270 | A1 | 11/2003 | Kung et al. |
| 2005/0065732 | A1 | 3/2005 | Tilton et al. |
| 2005/0196473 | A1 | 9/2005 | Cheng et al. |
| 2015/0110906 | A1 | 4/2015 | Liu et al. |

FOREIGN PATENT DOCUMENTS

| | | |
|---|---|---|
| AU | 2005201751 A1 | 5/2005 |
| CN | 1335892 A | 2/2002 |
| CN | 1386135 A | 12/2002 |
| CN | 101098705 A | 1/2008 |
| CN | 101730535 A | 6/2010 |
| JP | 2003521226 A | 7/2003 |
| JP | 2004500390 A | 1/2004 |
| JP | 2007319051 A | 12/2007 |
| JP | 2008519767 A | 6/2008 |
| WO | WO 0024934 A | 5/2000 |
| WO | 0166803 A2 | 9/2001 |
| WO | WO 0166803 A2 | 9/2001 |
| WO | 2008101079 A1 | 8/2008 |

OTHER PUBLICATIONS

Liu S-H et al., "Old formula, new Rx: The journey of PHY906 as cancer adjuvant therapy", Journal of Ethnopharmacology, vol. 140 (2012), pp. 614-623. (Year: 2012).*
International Search Report and Written Opinion for PCT International Application No. PCT/US2017/038421 dated Sep. 13, 2017.
Lam, et al.,Mechanism based quality control (MBQC) for the four-herb Chinese medicine formulation, PHY906 (YIV-906) and other herbal products, Cancer Research 77(13), Supplement ,Jul. 2017 ,3138.
Xiong, et al.,Biopotency Assays:an Integrated Application to Quality Control of Chinese Materia Medica, Chinese Herbal Medicines 6(4) ,2014 ,256-264.
Rong , et al., "Genome-wide Biological Response Fingerprinting (BioReF) of the Chinese Botanical Formulation ISF-1 Enables the Selection of Multiple Marker Genes as a Potential Metric for Quality Control", J Ethnopharmacol. 113(1), Aug. 2007, 35-44 (abstract only).
Ivanov , et al., "method of analyzing gene expression in developing medicaments from medicinal plant raw material", [on-line] [ found on Oct. 14, 2020]—found on the Internet: URL:http://file:///C:/Users/otd1559/Downloads/675-%D0%A2%D0%B5%D0%BA%D1%81%D1%82%20%D1%81%D1%82%D0%B0%D1%82%D1%8C%D0B8-2669-1-10-20141221%20(2).pdf, 2002, pp. 45-50 (partial translation).
Extended European Search Report for European Patent Application No. 17816092.5 dated Dec. 12, 2019.
Cao , et al., "Discovery of Cyclooxygenase Inhibitors From Medicinal Plants Used to Treat Inflammation", harmacol Res. 61(6), Jun. 2010, 519-524.
Lam , et al., "The Four-Herb Chinese Medicine PHY906 Reduces Chemotherapy-Induced Gastrointestinal Toxicity", Sci Transl Med. 2(45), Aug. 2010, 45ra59.
Tilton , et al., "A comprehensive platform for quality control of botanical drugs (PhytomicsQC): a case study of Huangqin Tang (HQT) and PHY906", Chin Med. 5, 2010, 30.

(Continued)

*Primary Examiner* — Satyendra K Singh
(74) *Attorney, Agent, or Firm* — Saul Ewing Arnstein & Lehr LLP; Kathryn Doyle

(57) ABSTRACT

The invention relates to methods of evaluating the quality of a batch of an herbal composition, the method comprising subjecting a test batch of the herbal composition to one or more biological analysis methods and comparing the results derived from the test batch to the results of a known batch of herbal composition which has a known in vivo effect.

8 Claims, 10 Drawing Sheets

Specification includes a Sequence Listing.

(56) References Cited

OTHER PUBLICATIONS

English Translation of National Intellectual Property Administration, PRC Search Report for Chinese Application No. 201780045872.1 dated Jun. 9, 2021.
English Translation of First Office Action Form issued by the National Intellectual Property Administration, PRC for Chinese Application No. 201780045872.1 dated Jun. 9, 2021.
English Abstract of Dai et al. "Journal of Logistics College of the Armed Police Force (Medical Edition)" 24 (Jun. 15, 2015): 9.
English Translation of Notice of Reasons for Rejection issued by the Japanese Patent Office for Japanese Application No. 2018-567035 dated May 24, 2021.

* cited by examiner

FIG. 1A

In vivo activities of PHY906

| Batch | Enhancement of CPT11 action | Body weight protection |
|-------|-----------------------------|------------------------|
| 6     | ++                          | ++                     |
| 10    | ++                          | ++                     |
| 11    | ++                          | ++                     |
| F     | +                           | -                      |

FIG. 1C

Similarity based on chemical profiles

| similarity | 6 | 10 | 11 | F |
|---|---|---|---|---|
| PHY906-6 | 1 | 0.93 | 0.935 | 0.958 |
| PHY906-10 | 0.93 | 1 | 0.954 | 0.951 |
| PHY906-11 | 0.935 | 0.954 | 1 | 0.911 |
| F | 0.958 | 0.951 | 0.911 | 1 |

FIG. 2B

Correlation coefficient of different batchs of PHY906 close to 1

| | PHY906-6 | PHY906-10 | PHY906-11 | F |
|---|---|---|---|---|
| PHY906-6 | 1 | 0.964 | 0.955 | 0.775 |
| PHY906-10 | 0.964 | 1 | 0.959 | 0.840 |
| PHY906-11 | 0.955 | 0.959 | 1 | 0.747 |
| F | 0.775 | 0.840 | 0.747 | 1 |

FIG. 3A

| | | PHY906-6 AVE ± SD | PHY906-10 AVE ± SD | PHY906-11 AVE ± SD | F AVE ± SD |
|---|---|---|---|---|---|
| Inflammation | ICAM | 2.1 ± 0.4 | 1.6 ± 0.2 | 1.6 ± 0.2 | 0.9 ± 0.1 |
| | IRF5 | 1.9 ± 0.1 | 1.7 ± 0.1 | 1.7 ± 0.2 | 1.2 ± 0.3 |
| Anti-oxidation | AKR1C1 | 6.4 ± 0.8 | 5.4 ± 0.9 | 5.3 ± 0.8 | 2.8 ± 1.2 |
| | HO1 | 1.7 ± 0.2 | 1.9 ± 0.2 | 1.6 ± 0.2 | 1.7 ± 0.2 |
| | GCLC | 5.1 ± 0.1 | 3.9 ± 0.2 | 4.0 ± 0.7 | 2.1 ± 0.7 |
| | GCLM | 9.3 ± 0.7 | 7.2 ± 0.4 | 7.9 ± 1.1 | 4.3 ± 1.3 |
| Growth and differentiation | Axin2 | 0.9 ± 0.3 | 0.8 ± 0.4 | 0.8 ± 0.2 | 0.6 ± 0.3 |
| | GDF15 | 35.9 ± 5.8 | 20.4 ± 1.5 | 20.5 ± 0.5 | 6.1 ± 2.5 |
| | IGFBP3 | 1.6 ± 0.8 | 1.5 ± 0.5 | 1.1 ± 0.1 | 1.5 ± 0.4 |
| | OKL38 | 6.0 ± 0.7 | 5.8 ± 0.7 | 5.7 ± 0.6 | 3.7 ± 0.2 |
| | PIM1 | 15.2 ± 2.7 | 7.4 ± 2.3 | 9.1 ± 4.1 | 3.3 ± 1.8 |
| | SERTAD | 3.0 ± 0.2 | 2.0 ± 0.2 | 2.2 ± 0.5 | 1.1 ± 0.3 |
| | SOS1 | 6.4 ± 1.1 | 9.8 ± 1.4 | 8.9 ± 1.5 | 9.1 ± 1.9 |
| Metabolism | BHMT2 | 1.5 ± 0.4 | 1.9 ± 0.4 | 1.8 ± 0.4 | 1.5 ± 0.3 |
| | CPT1A | 2.0 ± 0.6 | 2.2 ± 0.4 | 2.1 ± 0.4 | 1.7 ± 0.5 |
| | SLC7A11 | 11.6 ± 3.2 | 6.3 ± 1.3 | 6.6 ± 2.0 | 2.4 ± 0.6 |
| Cell-cell interaction and cytoskeleton | CD24 | 0.4 ± 0.2 | 0.3 ± 0.1 | 0.4 ± 0.1 | 0.3 ± 0.1 |
| | EMP2 | 2.0 ± 0.3 | 2.3 ± 0.4 | 2.2 ± 0.6 | 1.5 ± 1.0 |
| | KRT23 | 2.0 ± 0.1 | 2.0 ± 0.1 | 1.9 ± 0.2 | 1.0 ± 0.3 |

FIG. 3B

Correlation analysis

|  | PHY906-6 | PHY906-10 | PHY906-11 | F |
|---|---|---|---|---|
| PHY906-6 | 1 | 0.949 | 0.966 | 0.585 |
| PHY906-10 | 0.949 | 1 | 0.995 | 0.798 |
| PHY906-11 | 0.966 | 0.995 | 1 | 0.768 |
| F | 0.585 | 0.798 | 0.768 | 1 |

SEQUENCE LISTING

```
<160> NUMBER OF SEQ ID NOS: 55

<210> SEQ ID NO 1
<211> LENGTH: 68
<212> TYPE: DNA
<213> ORGANISM: Artificial Sequence
<220> FEATURE:
<223> OTHER INFORMATION: CRE agcctgacgt cagagag

<400> SEQUENCE: 1
agcctgacgt cagagagagc ctgacgtcag agagagcctg acgtcagaga gagcctgacg      60
tcagagag                                                              68

<210> SEQ ID NO 2
<211> LENGTH: 40
<212> TYPE: DNA
<213> ORGANISM: Artificial Sequence
<220> FEATURE:
<223> OTHER INFORMATION: NFkB Response Element DNA Sequence

<400> SEQUENCE: 2
gggaatttcc gggaatttcc gggaatttcc gggaatttcc                            40

<210> SEQ ID NO 3
<211> LENGTH: 40
<212> TYPE: DNA
<213> ORGANISM: Artificial Sequence
<220> FEATURE:
<223> OTHER INFORMATION: TLR2 Response Element DNA Sequence

<400> SEQUENCE: 3
gggaatttcc gggaatttcc gggaatttcc gggaatttcc                            40

<210> SEQ ID NO 4
<211> LENGTH: 40
<212> TYPE: DNA
<213> ORGANISM: Artificial Sequence
<220> FEATURE:
<223> OTHER INFORMATION: TLR4 Response Element DNA Sequence

<400> SEQUENCE: 4
gggaatttcc gggaatttcc gggaatttcc gggaatttcc                            40

<210> SEQ ID NO 5
<211> LENGTH: 90
<212> TYPE: DNA
<213> ORGANISM: Artificial Sequence
<220> FEATURE:
<223> OTHER INFORMATION: GAS / INF gamma Response Element DNA Sequence

<400> SEQUENCE: 5
atattactct aaatcatatt actctaaatc atattactct aaatcatatt actctaaatc      60
```
atattactct aaatcatatt actctaaatc         90

<210> SEQ ID NO 6
<211> LENGTH: 75
<212> TYPE: DNA
<213> ORGANISM: Artificial Sequence
<220> FEATURE:
<223> OTHER INFORMATION: IFN-a/B Response Element DNA Sequence

<400> SEQUENCE: 6
tagtttcact ttccctagtt tcactttccc tagtttcact ttccctagtt tcactttccc    60
tagtttcact ttccc         75

<210> SEQ ID NO 7
<211> LENGTH: 78
<212> TYPE: DNA
<213> ORGANISM: Artificial Sequence
<220> FEATURE:
<223> OTHER INFORMATION: STAT3 Response Element DNA Sequence

<400> SEQUENCE: 7
tgcattcccg taatgcattc ccgtaatgca ttcccgtaat gcattcccgt aatgcattcc    60
cgtaatgcat tcccgtaa         78

<210> SEQ ID NO 8
<211> LENGTH: 180
<212> TYPE: DNA
<213> ORGANISM: Artificial Sequence
<220> FEATURE:
<223> OTHER INFORMATION: Lefx12 Response Element DNA Sequence

<400> SEQUENCE: 8
agatcaaagg gggtaagatc aaaggggggta agatcaaagg gggtaagatc aaaggggggta    60 agatcaaagg gggtaagatc aaaggggggta agatcaaagg gggtaagatc aaaggggggta   120 agatcaaagg gggtaagatc aaaggggggta agatcaaagg gggtaagatc aaaggggggta   180

<210> SEQ ID NO 9
<211> LENGTH: 60
<212> TYPE: DNA
<213> ORGANISM: Artificial Sequence
<220> FEATURE:
<223> OTHER INFORMATION: TGFbx4 Response Element DNA Sequence

<400> SEQUENCE: 9
gagtatgtct agactgagta tgtctagact gagtatgtct agactgagta tgtctagact    60

<210> SEQ ID NO 10
<211> LENGTH: 60
<212> TYPE: DNA
<213> ORGANISM: Artificial Sequence
<220> FEATURE:
<223> OTHER INFORMATION: ER-a Response Element DNA Sequence

<400> SEQUENCE: 10
ggtcacagtg acctaggtca cagtgaccta ggtcacagtg acctaggtca cagtgaccta    60

<210> SEQ ID NO 11
<211> LENGTH: 60
<212> TYPE: DNA
<213> ORGANISM: Artificial Sequence
<220> FEATURE:
<223> OTHER INFORMATION: ER-b Response Element DNA Sequence

<400> SEQUENCE: 11

```
ggtcacagtg acctaggtca cagtgaccta ggtcacagtg acctaggtca cagtgaccta        60

<210> SEQ ID NO 12
<211> LENGTH: 72
<212> TYPE: DNA
<213> ORGANISM: Artificial Sequence
<220> FEATURE:
<223> OTHER INFORMATION: VDR Response Element DNA Sequence

<400> SEQUENCE: 12
gatccacaag gttcacgagg ttcagatcca caaggttcac gaggttcaga tccacaaggt        60
tcacgaggtt ca                                                           72

<210> SEQ ID NO 13
<211> LENGTH: 60
<212> TYPE: DNA
<213> ORGANISM: Artificial Sequence
<220> FEATURE:
<223> OTHER INFORMATION: PRE Response Element DNA Sequence

<400> SEQUENCE: 13
gggacatggt gttctgggac atggtgttct gggacatggt gttctgggac atggtgttct        60

<210> SEQ ID NO 14
<211> LENGTH: 60
<212> TYPE: DNA
<213> ORGANISM: Artificial Sequence
<220> FEATURE:
<223> OTHER INFORMATION: MR Response Element DNA Sequence

<400> SEQUENCE: 14
ggtacatttt gttctggtac attttgttct ggtacatttt gttctggtac attttgttct        60

<210> SEQ ID NO 15
<211> LENGTH: 84
<212> TYPE: DNA
<213> ORGANISM: Artificial Sequence
<220> FEATURE:
<223> OTHER INFORMATION: NRF2 Response Element DNA Sequence

<400> SEQUENCE: 15
tcacagtgac tcagcaaaat ttcacagtga ctcagcaaaa tttcacagtg actcagcaaa        60
atttcacagt gactcagcaa aatt                                              84

<210> SEQ ID NO 16
<211> LENGTH: 18
<212> TYPE: DNA
<213> ORGANISM: Artificial Sequence
<220> FEATURE:
<223> OTHER INFORMATION: ICAM forward primer

<400> SEQUENCE: 16
tatggcaacg actccttc                                                     18

<210> SEQ ID NO 17
<211> LENGTH: 18
<212> TYPE: DNA
<213> ORGANISM: Artificial Sequence
<220> FEATURE:
<223> OTHER INFORMATION: ICAM reverse primer

<400> SEQUENCE: 17
cattcagcgt caccttgg                                                     18
```

<210> SEQ ID NO 18
<211> LENGTH: 25
<212> TYPE: DNA
<213> ORGANISM: Artificial Sequence
<220> FEATURE:
<223> OTHER INFORMATION: IRF5 forward primer

<400> SEQUENCE: 18
atgctgcctc tgaccgacct ggaga                                              25

<210> SEQ ID NO 19
<211> LENGTH: 25
<212> TYPE: DNA
<213> ORGANISM: Artificial Sequence
<220> FEATURE:
<223> OTHER INFORMATION: IRF5 reverse primer

<400> SEQUENCE: 19
cttgctccag gcttatgggg ccgaa                                              25

<210> SEQ ID NO 20
<211> LENGTH: 21
<212> TYPE: DNA
<213> ORGANISM: Artificial Sequence
<220> FEATURE:
<223> OTHER INFORMATION: AKR1C1 forward primer

<400> SEQUENCE: 20
ccagagcact ataggcaacc a                                                  21

<210> SEQ ID NO 21
<211> LENGTH: 20
<212> TYPE: DNA
<213> ORGANISM: Artificial Sequence
<220> FEATURE:
<223> OTHER INFORMATION: AKR1C1 reverse primer

<400> SEQUENCE: 21
aacaagccag ggctcaagta                                                    20

<210> SEQ ID NO 22
<211> LENGTH: 24
<212> TYPE: DNA
<213> ORGANISM: Artificial Sequence
<220> FEATURE:
<223> OTHER INFORMATION: HO1 forward primer

<400> SEQUENCE: 22
tcctgctcaa catccagctc tttg                                               24

<210> SEQ ID NO 23
<211> LENGTH: 23
<212> TYPE: DNA
<213> ORGANISM: Artificial Sequence
<220> FEATURE:
<223> OTHER INFORMATION: HO1 reverse primer

<400> SEQUENCE: 23
gggcagaatc ttgcactttg ttg                                                23

<210> SEQ ID NO 24
<211> LENGTH: 20
<212> TYPE: DNA
<213> ORGANISM: Artificial Sequence
<220> FEATURE:
<223> OTHER INFORMATION: GCLC forward primer

```
<400> SEQUENCE: 24
ctttctcccc agacaggacc                                                     20

<210> SEQ ID NO 25
<211> LENGTH: 20
<212> TYPE: DNA
<213> ORGANISM: Artificial Sequence
<220> FEATURE:
<223> OTHER INFORMATION: GCLC reverse primer

<400> SEQUENCE: 25
caaggacgtt ctcaagtggg                                                     20

<210> SEQ ID NO 26
<211> LENGTH: 23
<212> TYPE: DNA
<213> ORGANISM: Artificial Sequence
<220> FEATURE:
<223> OTHER INFORMATION: GCLM forward primer

<400> SEQUENCE: 26
gtatcagtgg gcacaggtaa aac                                                 23

<210> SEQ ID NO 27
<211> LENGTH: 22
<212> TYPE: DNA
<213> ORGANISM: Artificial Sequence
<220> FEATURE:
<223> OTHER INFORMATION: GCLM reverse primer

<400> SEQUENCE: 27
cttgcttcag aaagcagttc tt                                                  22

<210> SEQ ID NO 28
<211> LENGTH: 22
<212> TYPE: DNA
<213> ORGANISM: Artificial Sequence
<220> FEATURE:
<223> OTHER INFORMATION: Axin2 forward primer

<400> SEQUENCE: 28
ctggctccag aagatcacaa ag                                                  22

<210> SEQ ID NO 29
<211> LENGTH: 21
<212> TYPE: DNA
<213> ORGANISM: Artificial Sequence
<220> FEATURE:
<223> OTHER INFORMATION: Axin2 reverse primer

<400> SEQUENCE: 29
atctcctcaa acaccgctcc a                                                   21

<210> SEQ ID NO 30
<211> LENGTH: 25
<212> TYPE: DNA
<213> ORGANISM: Artificial Sequence
<220> FEATURE:
<223> OTHER INFORMATION: GDF15 forward primer

<400> SEQUENCE: 30
ctccgaagac tccagattcc gagag                                               25

<210> SEQ ID NO 31
```

```
<211> LENGTH: 24
<212> TYPE: DNA
<213> ORGANISM: Artificial Sequence
<220> FEATURE:
<223> OTHER INFORMATION: GDF15 reverse primer

<400> SEQUENCE: 31
cagccgcact tctggcgtga gtat                                              24

<210> SEQ ID NO 32
<211> LENGTH: 25
<212> TYPE: DNA
<213> ORGANISM: Artificial Sequence
<220> FEATURE:
<223> OTHER INFORMATION: IGFBP3 forward primer

<400> SEQUENCE: 32
ccagcgccgc cagctccagg aaatg                                             25

<210> SEQ ID NO 33
<211> LENGTH: 25
<212> TYPE: DNA
<213> ORGANISM: Artificial Sequence
<220> FEATURE:
<223> OTHER INFORMATION: IGFBP3 reverse primer

<400> SEQUENCE: 33
cctttcttga tgatgattat ctttg                                             25

<210> SEQ ID NO 34
<211> LENGTH: 24
<212> TYPE: DNA
<213> ORGANISM: Artificial Sequence
<220> FEATURE:
<223> OTHER INFORMATION: OKL38 forward primer

<400> SEQUENCE: 34
ctcccggtca tcattgtggg taac                                              24

<210> SEQ ID NO 35
<211> LENGTH: 22
<212> TYPE: DNA
<213> ORGANISM: Artificial Sequence
<220> FEATURE:
<223> OTHER INFORMATION: OKL38 reverse primer

<400> SEQUENCE: 35
ggtagtccag gtcctggtcc ag                                                22

<210> SEQ ID NO 36
<211> LENGTH: 25
<212> TYPE: DNA
<213> ORGANISM: Artificial Sequence
<220> FEATURE:
<223> OTHER INFORMATION: PIM1 forward primer

<400> SEQUENCE: 36
caccaagctg gcgcccggca aggag                                             25

<210> SEQ ID NO 37
<211> LENGTH: 24
<212> TYPE: DNA
<213> ORGANISM: Artificial Sequence
<220> FEATURE:
<223> OTHER INFORMATION: PIM1 reverse primer

<400> SEQUENCE: 37
```

-continued acgtgtttga tggccaccgg caag                                    24

<210> SEQ ID NO 38
<211> LENGTH: 25
<212> TYPE: DNA
<213> ORGANISM: Artificial Sequence
<220> FEATURE:
<223> OTHER INFORMATION: SERTAD forward primer

<400> SEQUENCE: 38
ggaggagaag gaacctctgg cagtc                                   25

<210> SEQ ID NO 39
<211> LENGTH: 25
<212> TYPE: DNA
<213> ORGANISM: Artificial Sequence
<220> FEATURE:
<223> OTHER INFORMATION: SERTAD reverse primer

<400> SEQUENCE: 39
actctgctgc aggctgtggt ggagc                                   25

<210> SEQ ID NO 40
<211> LENGTH: 25
<212> TYPE: DNA
<213> ORGANISM: Artificial Sequence
<220> FEATURE:
<223> OTHER INFORMATION: SOS1 forward primer

<400> SEQUENCE: 40
tactttgaac ttttgaagca gttag                                   25

<210> SEQ ID NO 41
<211> LENGTH: 25
<212> TYPE: DNA
<213> ORGANISM: Artificial Sequence
<220> FEATURE:
<223> OTHER INFORMATION: SOS1 reverse primer

<400> SEQUENCE: 41
aaccgacatg cagattcact cagtc                                   25

<210> SEQ ID NO 42
<211> LENGTH: 23
<212> TYPE: DNA
<213> ORGANISM: Artificial Sequence
<220> FEATURE:
<223> OTHER INFORMATION: CPT1A forward primer

<400> SEQUENCE: 42
ccaccaagat ctggatgggt atg                                     23

<210> SEQ ID NO 43
<211> LENGTH: 24
<212> TYPE: DNA
<213> ORGANISM: Artificial Sequence
<220> FEATURE:
<223> OTHER INFORMATION: CPT1A reverse primer

<400> SEQUENCE: 43
caccgactgt agatacctgt tcac                                    24

<210> SEQ ID NO 44
<211> LENGTH: 25
<212> TYPE: DNA

<213> ORGANISM: Artificial Sequence
<220> FEATURE:
<223> OTHER INFORMATION: SLC7A11 forward primer

<400> SEQUENCE: 44
gtggggtcct gtcactattt ggagc                                    25

<210> SEQ ID NO 45
<211> LENGTH: 25
<212> TYPE: DNA
<213> ORGANISM: Artificial Sequence
<220> FEATURE:
<223> OTHER INFORMATION: SLC7A11 reverse primer

<400> SEQUENCE: 45
agcagtagct gcagggcgta ttatg                                    25

<210> SEQ ID NO 46
<211> LENGTH: 23
<212> TYPE: DNA
<213> ORGANISM: Artificial Sequence
<220> FEATURE:
<223> OTHER INFORMATION: BHMT2 forward primer

<400> SEQUENCE: 46
ctttggactg gagtccagag ttg                                      23

<210> SEQ ID NO 47
<211> LENGTH: 23
<212> TYPE: DNA
<213> ORGANISM: Artificial Sequence
<220> FEATURE:
<223> OTHER INFORMATION: BHMT2 reverse primer

<400> SEQUENCE: 47
atactccctt cgagcccttg ctc                                      23

<210> SEQ ID NO 48
<211> LENGTH: 23
<212> TYPE: DNA
<213> ORGANISM: Artificial Sequence
<220> FEATURE:
<223> OTHER INFORMATION: CD24 forward primer

<400> SEQUENCE: 48
actgctccta cccacgcaga ttt                                      23

<210> SEQ ID NO 49
<211> LENGTH: 22
<212> TYPE: DNA
<213> ORGANISM: Artificial Sequence
<220> FEATURE:
<223> OTHER INFORMATION: CD24 reverse primer

<400> SEQUENCE: 49
cacgaagaga ctggctgttg ac                                       22

<210> SEQ ID NO 50
<211> LENGTH: 27
<212> TYPE: DNA
<213> ORGANISM: Artificial Sequence
<220> FEATURE:
<223> OTHER INFORMATION: EMP2 forward primer

<400> SEQUENCE: 50
gttcattgcc accgtcgaca atgcctg                                  27

```
<210> SEQ ID NO 51
<211> LENGTH: 25
<212> TYPE: DNA
<213> ORGANISM: Artificial Sequence
<220> FEATURE:
<223> OTHER INFORMATION: EMP2 reverse primer

<400> SEQUENCE: 51
gcagcgtgga gtactcttga aagct                                             25

<210> SEQ ID NO 52
<211> LENGTH: 26
<212> TYPE: DNA
<213> ORGANISM: Artificial Sequence
<220> FEATURE:
<223> OTHER INFORMATION: KRT23 forward primer

<400> SEQUENCE: 52
ctgcagacac agtacagcac gaaatc                                            26

<210> SEQ ID NO 53
<211> LENGTH: 26
<212> TYPE: DNA
<213> ORGANISM: Artificial Sequence
<220> FEATURE:
<223> OTHER INFORMATION: KRT23 reverse primer

<400> SEQUENCE: 53
ctttgattct tcccgtgtcc cttcac                                            26

<210> SEQ ID NO 54
<211> LENGTH: 21
<212> TYPE: DNA
<213> ORGANISM: Artificial Sequence
<220> FEATURE:
<223> OTHER INFORMATION: Actin forward primer

<400> SEQUENCE: 54
gccacggctg cttccagctc c                                                 21

<210> SEQ ID NO 55
<211> LENGTH: 24
<212> TYPE: DNA
<213> ORGANISM: Artificial Sequence
<220> FEATURE:
<223> OTHER INFORMATION: Actin reverse primer

<400> SEQUENCE: 55
ttgtgctggg tgccagggca gtga                                              24
```

MECHANISM BASED QUALITY CONTROL FOR BOTANICAL MEDICINE

CROSS-REFERENCE TO RELATED APPLICATIONS

This application is a 35 U.S.C. § 371 national phase application from, and claims priority to, International Application No. PCT/US2017/038421, filed Jun. 21, 2017, and published under PCT Article 21(2) in English, which claims priority under 35 U.S.C. § 119(e) to U.S. Provisional Application No. 62/353,313, filed Jun. 22, 2016, all of which are incorporated herein by reference in their entireties.

STATEMENT REGARDING FEDERALLY SPONSORED RESEARCH OR DEVELOPMENT

This invention was made with government support under CA154295 awarded by National Institutes of Health (NIH). The government has certain rights in the invention.

BACKGROUND OF THE INVENTION

Herbal and botanical medicines have been used by people around the world for centuries. Today, herbal compositions, herbal extracts and compounds isolated from herbs play an important role in the treatment of a range of diseases and disorders and many of today's most commonly used medicines, such as aspirin, started as herbal remedies.

In order to reliably use botanical medicines for the treatment of disease, strict quality control is important. Unlike synthetic medicinal compositions, which can be more easily controlled and formulated, botanical medicines are derived from biologically derived plant matter. Each plant can contain a range of compounds in varied concentrations depending on genetic variation, growing conditions, the timing of planting and harvesting and the age of the plant matter when the botanical medicine is prepared.

Due to this variation, it is commonly observed that different batches of the same botanical medicine can have varied in vivo activity, depending on the diversity of the individual plants as well as variations in the preparation methods. It is also often observed that despite varied in vivo activity, different batches of an herbal medicine can still share very similar chemical profiles by standard chemical analysis methods such as chromatography and mass spectrometry. It is possible that slight impurities or compositional variations which cannot be detected through these chemical analysis methods can have a drastic effect on the overall activity of the botanical medicine. Thus, it is difficult to determine whether a specific batch of an herbal composition will have the desired in vivo activity simply through chemical analysis methods.

PHY906 is an herbal mixture extract based on the Huang Qin Tang herbal mixture, which was first described in Chinese texts 1,800 years ago, and has been used to treat gastrointestinal symptoms. PHY906 is composed of four herbs: *Scutellaria baicalensis* (S), *Glycyrrhiza uralensis* (G), *Paeonia lactiflora* (P), and *Ziziphus jujuba* (Z). PHY906 is currently manufactured according to cGMP (current Good Manufacturing Practice). In clinical trials, PHY906 is shown to enhance the therapeutic index of chemotherapy against cancer.

There is thus an unmet need in the art for methods of determining the quality and potential efficacy of botanical medicines and other herbal compositions which do not rely solely on chemical analysis. The present invention satisfies this unmet need.

SUMMARY OF THE INVENTION

The present invention includes a method of evaluating the quality and potential in vivo activity of a test batch of an herbal composition, the method comprising subjecting the test batch of the herbal composition to one or more biological analysis methods selected from:
(a) a signaling transduction activity response assay; and
(b) a gene expression assay;
and then comparing the test batch results of the biological analysis method with results derived from a known batch of an herbal composition which has a known level of in vivo activity;
wherein a measurement of the difference between the test batch results and the known batch results provides an evaluation of the quality and potential in vivo activity of the test batch herbal composition.

In certain embodiments, the herbal composition comprises one or more compositions selected from the group consisting of herbal extracts of *Scutellaria baicalensis* (S), *Glycyrrhiza uralensis* (G), *Paeonia lactiflora* (P), and *Ziziphus jujuba* (Z), any fractions thereof and any active chemicals present in the herbal extracts or fractions thereof. In other embodiments, the herbal composition is PHY906, wherein PHY906 comprises herbal extracts of *Scutellaria baicalensis* (S), *Glycyrrhiza uralensis* (G), *Paeonia lactiflora* (P), and *Ziziphus jujuba* (Z) in a 3:2:2:2 (S:G:P:Z) ratio.

In certain embodiments, the signal transduction activity response assay comprises one or more assays selected from the group consisting of luciferase reporter assays and enzymatic assays.

In certain embodiments, the signal transduction activity response assay comprises measurement of signal transduction activity response against one or more enzymes selected from inflammation enzymes, cell growth and differentiation enzymes and endocrine and hormone enzymes. In other embodiments, the signal transduction activity response assay comprises measuring the signal transduction activity response against one or more signaling pathways selected from the group consisting of TNFa-NFkB, TLR2-NFkB, TLR4-NFkB, IL6-stat3, IFNg-stat1/1, IFNa-stat1/2, DEX-GR, COX-2, iNOS, NRF2, TGFb-Smad2/3, TPA-AP1, CREB, wnt3a-Lef/b-cat, VD3-VDR, ER-alpha, ER-beta, DHT-AR and aldosterone-MR.

In certain embodiments, the gene expression assay comprises: treating HepG2 cells with the herbal composition for 24 h, extracting the mRNA produced and quantifying the mRNA through qRT-PCR analysis.

In certain embodiments, the gene expression assay comprises measurement of one or more genes encoding proteins having a function selected from inflammation, anti-oxidation, growth and differentiation, metabolism, and cell-cell interaction. In other embodiments, the one or more genes are selected from the group consisting of ICAM, IRF5, AKR1C1, HO1, GCLC, GCLM, Axin2, GDF15, IGFBP3, OKL38, PIM1, SERTAD, SOS1, BHMT2, CPT1A, SLC7A11, CD24, EMP2 and KRT23.

In certain embodiments, the one or more biological analysis methods differentiate between active batches of the herbal composition and inactive batches of the herbal composition better than chemical composition analysis methods.

In other embodiments, the chemical composition analysis methods include LC-MS (liquid chromatography-mass spectrometry).

In certain embodiments, if the test batch results are between about 90% and about 110% of the known batch results then the test batch is determined to have sufficiently similar quality as the known batch and potential in vivo activity.

In certain embodiments, the quality of the test batch of the herbal composition is further analyzed by LC-MS.

The invention further provides a method of treating a subject with cancer, the method comprising evaluating the quality and potential in vivo efficacy of a test batch of PHY906 by subjecting the herbal composition to one or more biological analysis methods selected from:
(a) a signaling transduction activity response assay; and
(b) a gene expression assay;
comparing the results of the biological analysis method with results derived from a known batch of PHY906 which has a known level of in vivo activity;
wherein a measurement of the difference between the test batch results and the known batch results provides an evaluation of the quality and potential in vivo activity of the test batch herbal composition,
and if the test batch of PHY906 shows similar activity in the biological analysis methods to the known batch of PHY906, administer the test batch of PHY906 to the subject.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIGS. 1A-1D illustrate a comparison between in vivo activities and chemical similarity among different batches of PHY 906 and F (a commercial Huang Qin Tang extract mixture). The results depicted indicate a lack of correlation between chemical analysis and biological effect. FIG. 1A reports the effects of different batches of PHY906 and F on the anti-tumor activity of CPT11 and body weight protection of BDF1 mice bearing colon tumors. FIG. 1B reports a chemical similarity analysis of PHY906 detected by LC-MS. FIG. 1C is a table reporting chemical similarity among different batches of PHY906 and F where "1" represents an identical chemical profile and "0" represents a completely different chemical profile with no overlap. FIG. 1D reports the information in FIG. 1C as a clustering analysis based on chemical profiles.

FIGS. 2A-2C report the signal transduction activity response analysis among different batches of PHY906 and F. The results depicted indicate a close correlation between transduction activity response and biological activity. FIG. 2A reports the effect of different batches of PHY906 and F on signal transduction activity response using different luciferase reporter cell lines and enzyme assays. FIG. 2B is a table reporting a correlation analysis of the signal transduction activity response for different batches of PHY906 and F where "1" represents identical signal transduction activity and "0" represents completely dissimilar signal transduction activity. FIG. 2C reports the information in FIG. 2B as a clustering analysis based on signal transduction activity response.

FIGS. 3A-3C report the gene expression analysis among different batches of PHY906 and F. The results depicted indicate a close correlation between gene expression and biological activity. FIG. 3A reports the effect of different batches of PHY906 and F on select gene expression. HepG2 cells were treated with PHY906 or F for 24 h and mRNA was extracted for qRT-PCR analysis. FIG. 3B is a table reporting a correlation analysis of the gene expression for PHY906 and F where "1" represents identical gene expression and "0" represents completely dissimilar gene expression. FIG. 3C reports the information in FIG. 3B as a clustering analysis based on gene expression.

DETAILED DESCRIPTION OF THE INVENTION

Figure 1B:
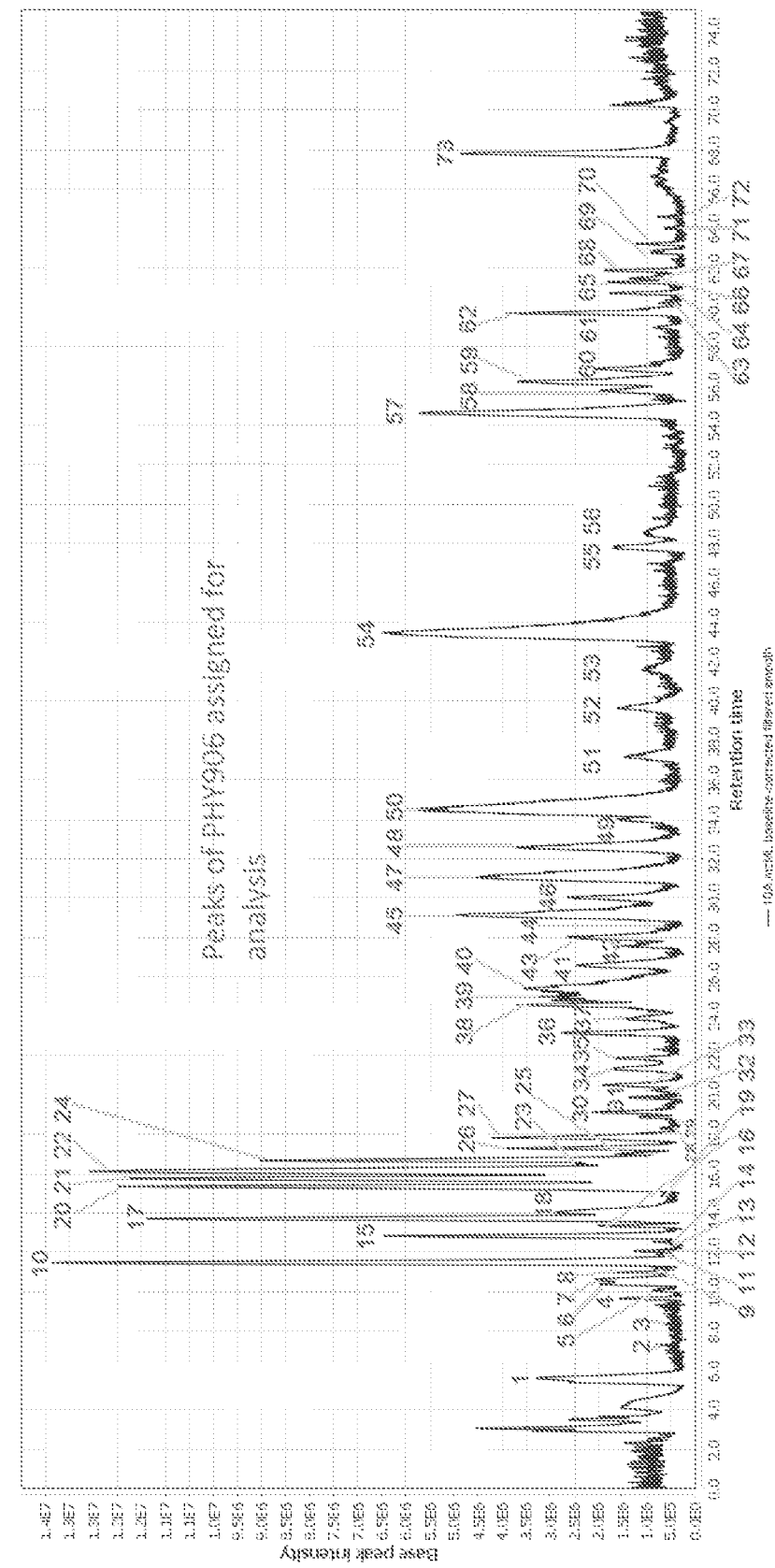

The invention relates in one aspect to the unexpected discovery that herbal compositions with nearly identical chemical analysis profiles can have highly varied in vivo activity. The invention further relates to the unexpected discovery that biological assays, including signaling transduction activity response assays and gene expression assays are better predictors of the potential in vivo activity of an herbal composition than chemical analysis profiles.

In certain embodiments, the invention relates to methods of evaluating the quality of a batch of an herbal composition, the method comprising subjecting the herbal composition to one or more biological analysis methods. In certain embodiments, the herbal composition comprises one or more compositions selected from the group consisting of herbal extracts of *Scutellaria baicalensis* (S), *Glycyrrhiza uralensis* (G), *Paeonia lactiflora* (P), and *Ziziphus jujuba* (Z), any fractions thereof and any active chemicals present in the herbal extracts or fractions thereof.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in pharmacology, natural product chemistry, and organic chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "cancer" is defined as disease characterized by the rapid and uncontrolled growth of aberrant cells. Cancer cells can spread locally or through the bloodstream and lymphatic system to other parts of the body. Examples of various cancers include but are not limited to, bone cancer, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "extract" refers to a concentrated preparation or solution of a compound or drug derived from a naturally occurring source, such as an herb or other plant material. Extracts may be prepared by a number of processes, including steeping an herb in solution, or drying and grinding an herb into a powder and dissolving the powder in a solution. An extract may be further concentrated by removing a portion of the solvent after dissolving an amount of the desired compound in the solution. An extract may also be strained or centrifuged to remove any solid material from the solution.

As used herein, the term "Huang Qin Tang" refers to an herbal composition comprising *Glycyrrhiza uralensis* Fisch (G), *Paeonia lactiflora* Pall (P), *Scutellaria baicalensis* Georgi (S), and *Ziziphus jujuba* Mill (Z). Huang Qin Tang can be in a number of different formulations, including PHY906 and F.

The phrase "inhibit," as used herein, means to reduce a molecule, a reaction, an interaction, a gene and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein or a gene's stability, expression, function and activity, e.g., antagonists.

As used herein, the term "PHY906" refers to a specific herbal composition comprising *Glycyrrhiza uralensis* Fisch (G), *Paeonia lactiflora* Pall (P), *Scutellaria baicalensis* Georgi (S), and *Ziziphus jujuba* Mill (Z). PHY906 can refer to, for example, a specific composition comprising S, G, P and Z in a 3:2:2:2 ratio prepared under standard operational procedure.

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the term "therapeutically effective amount" is an amount of a compound of the invention, that when administered to a patient, treats, minimizes and/or ameliorates a symptom of the disease or disorder. The amount of a compound of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

As used herein, the term "treatment" or "treating" is defined as the application or administration of a therapeutic agent, i.e., a compound useful within the invention (alone or in combination with another pharmaceutical agent), to a subject, or application or administration of a therapeutic agent to an isolated tissue or cell line from a subject (e.g., for diagnosis or ex vivo applications), who has cancer, a symptom of cancer or the potential to develop cancer, with the purpose to cure, heal, alleviate, relieve, alter, remedy, ameliorate, improve or affect cancer, the symptoms of cancer or the potential to develop cancer. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

The following abbreviations are used herein:
cGMP current Good Manufacturing Practice
F A commercial formulation of Huang Qin Tang
G *Glycyrrhiza uralensis* Fisch, also known as Chinese liquorice
HQT Huang Qin Tang
P *Paeonia laciflora* Pall, also known as Chinese peony
PCR Polymerase Chain Reaction
qRT-PCR Quantitative Reverse Transcription Polymerase Chain Reaction
S *Scutellaria baicalensis* Georgi, also known as Baikal skullcap or scute
STAR Signaling Transduction Activity Response
Z *Ziziphus jujube* Mill, also known as red date or Chinese date Quality Determination Methods The invention includes methods of evaluating the quality and potential in vivo efficacy of a batch of an herbal composition, the method comprising subjecting the herbal composition to one or more biological analysis methods selected from:

(a) a signaling transduction activity response assay; and
(b) a gene expression assay;

and then comparing the results of the biological analysis method with results derived from a batch of an herbal composition which has a known level of in vivo activity, wherein a measurement of the difference between the test batch results and the known batch results provides an evaluation of the quality and potential in vivo activity of the test batch herbal composition.

In certain embodiments, the herbal composition comprises one or more compositions selected from the group consisting of herbal extracts of *Scutellaria baicalensis* (S), *Glycyrrhiza uralensis* (G), *Paeonia lactiflora* (P), and *Ziziphus jujuba* (Z), any fractions thereof and any active chemicals present in the herbal extracts or fractions thereof. In other embodiments the herbal composition is PHY906, wherein PHY906 comprises herbal extracts of *Scutellaria baicalensis* (S), *Glycyrrhiza uralensis* (G), *Paeonia lactiflora* (P), and *Ziziphus jujuba* (Z) in a 3:2:2:2 (S:G:P:Z) ratio. In other embodiments, the herbal composition can comprise a composition or extract derived from any other botanical or herbal source, any fractions thereof, or any active chemicals present in the botanical or herbal source or fractions thereof.

In certain embodiments, the quality and potential efficacy of the test batch of the herbal composition can be determined through a signal transduction activity response assay selected from one or more luciferase reporter assays and/or enzymatic assays. In other embodiments, the signal transduction activity response assay measures the signal transduction activity response against one or more signaling pathways selected from the group consisting of TNFa-NFkB, TLR2-NFkB, TLR4-NFkB, IL6-stat3, IFNg-stat1/1, IFNa-stat1/2, DEX-GR, COX-2, iNOS, NRF2, TGFb-Smad2/3, TPA-AP1, CREB, wnt3a-Lef/b-cat, VD3-VDR, ER-alpha, ER-beta, DHT-AR and aldosterone-MR.

In certain embodiments, the quality and potential efficacy of the test batch of the herbal composition can be determined through a gene expression assay, the assay comprises treating HepG2 cells with the herbal composition for about 24 h, extracting the mRNA produced and quantifying the mRNA through qRT-PCR analysis. In other embodiments, the gene expression is measured for one or more genes encoding proteins responsible for a function selected from inflammation, anti-oxidation, growth and differentiation, metabolism, and cell-cell interaction. In yet other embodiments, the gene expression is measured for one or more genes selected from the group consisting of ICAM, IRF5, AKR1C1, HO1, GCLC, GCLM, Axin2, GDF15, IGFBP3, OKL38, PIM1, SERTAD, SOS1, BHMT2, CPT1A, SLC7A11, CD24, EMP2 and KRT23.

In certain embodiments, the biological analysis methods of the invention more accurately differentiate active batches of the herbal composition from inactive batches of the herbal composition than chemical composition analysis methods. In certain embodiments, active batches of the herbal composition are more strongly correlated to one another by the results of the biological assays of the invention than by standard chemical analysis methods. In certain embodiments, the methods of the invention can differentiate active batches of the herbal composition from inactive batches of the herbal composition, even when they share chemical analysis profiles with greater than 90% similarity. In other embodiments, the biological analysis methods distinguish active batches of the herbal composition from inactive batches of the herbal composition better than chemical composition analysis methods. In other embodiments, the test batch is considered to have sufficiently similar quality and potential in vivo activity if he test batch results are between about 85% and about 115% of the known batch results. In other embodiments, the test batch is considered to have sufficiently similar quality and potential in vivo activity if he test batch results are between about 90% and about 110% of the known batch results. In other embodiments, the test batch is considered to have sufficiently similar quality and potential in vivo activity if he test batch results are between about 95% and about 105% of the known batch results.

In certain embodiments, the method of the invention further comprises analyzing the batch of the herbal composition by LC-MS.

In certain embodiments, the methods of the invention can be used to determine the quality and/or potential in vivo efficacy of a batch of any herbal or botanical composition.

Treatment Methods

The invention also provides methods of treating a subject with cancer, the method comprising evaluating the quality and potential in vivo efficacy of a test batch of PHY906 by subjecting the herbal composition to one or more biological analysis methods selected from:
 (a) a signaling transduction activity response assay; and
 (b) a gene expression assay;
 comparing the results of the biological analysis method with results derived from a known batch of PHY906 which has a known level of in vivo activity; and if the test batch of PHY906 shows similar activity in the biological analysis methods to the known batch of PHY906, administer the test batch of PHY906 to the subject.

In certain embodiments, the treatment methods of the invention can be adapted for any known botanical or herbal composition or medicine. In other embodiments, the treatment methods of the invention can be adapted for the treatment of other diseases or disorders.

Kits

The invention also relates to kits for determining the quality and potential in vivo activity of a batch of an herbal composition. In certain embodiments, the kit comprises one or more biological assay materials selected from a signaling transduction activity response assay and a gene expression assay. In other embodiments the kit further comprises instructions for determining the quality and potential in vivo activity of a batch of an herbal composition using the assays of the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Materials and Methods

Preparation of Herbal Extracts

PHY906 is comprised of a traditional hot water extract of four herbs, *Scutelleria baicalensis* Georgi (S), *Paeonia lactiflora* Pall. (P), *Glycyrrhiza uralensis* Fisch. (G), and *Ziziphus jujuba* Mill (Z), in the ratio of 3:2:2:2, respectively, and prepared under standard operational procedure. This extract comprises a complex mixture of multiple phytochemicals with multiple biological and pharmacological properties. At this time, it is not possible to identify the subset of relevant biologically active phytochemicals from the entire mixture. For this reason, high level chemical and biological metrics were used to characterize the PHY906 product.

The raw ingredients of PHY906 are pre-selected to meet rigid specifications set by PHYTOCEUTICA™ for acceptance by the herbal manufacturer, Sun Ten Pharmaceuticals in Taiwan.

Dried PHY906 (100 mg) was dissolved in one mL of 80° C. water. The mixture was vortexed for one minute, placed in an 80° C. water bath for 30 additional minutes with one minute of vortexing for every ten minutes. The sample was then cooled in a water bath of ambient temperature for five minutes, centrifuged for ten minutes at 10,000 rpm (Eppendorf Model 5810R, USA) and the resulting supernatant was filter (0.2 µm) sterilized. For subsequent LC/MS analysis, a 20 µL aliquot of this light brown extract was diluted with 980 µL of water. The final nominal concentration after extraction and dilution was 2 mg of dry weight PHY906 powder extract per mL of water. For biological experiments, the 100 mg/mL nominal concentration solution stock was diluted in the appropriate buffer or medium to the required final concentration.

The PHY906 extract is comprised of greater than 75% low molecular weight phytochemical compounds less than 1000 amu, 10% macromolecular components including protein, nucleic acid, complex carbohydrates, and 5% water. In addition, 10% by weight of excipient insoluble cellulose is added during a spray dry step in manufacturing. Heavy metals (Pb, Hg, Cd, As) concentrations are all less than 0.5 ppm, with mercury and cadmium less than 0.03 ppm, as detected by atomic absorption measurements. Pesticides levels (BHCs, DDTs, PCNB) concentrations are less than 0.2 ppm by LC-MS or GC-MS. Total bacteria counts are 260 cfu/g while E. coli and Salmonella species are not detected. Over 90% by weight of PHY906, excluding water content (5%) and insoluble starch excipient (10%), can be re-extracted. The final PHY906 liquid extract (100 mg/ml) is stable for 18 hours at room temperature and the properly stored bulk dry extract (vacuum packed, light tight and 4° C.) appears to be stable for more than three years. More detailed information about PHY906 can be found in: Lam W, Bussom S, Guan F, Jiang Z, Zhang W, Gullen E A, Liu S H, Cheng Y C, 2010, "The Four-Herb Chinese Medicine PHY906 Reduces Chemotherapy-Induced Gastrointestinal Toxicity", Sci. Transl. Med. 2(45):45ra59.

In Vivo Mouse Models

Murine Colon 38 cells (1-2×106 cells in 0.1 ml phosphate-buffered saline, PBS) were transplanted subcutaneously into four- to six-week-old female BDF1 mice (Charles River Laboratories). After 10 to 14 days, mice with tumor sizes of 150-300 mm³ were selected. Unless otherwise indicated, treatment groups each consisted of five mice. Tumor size, body weight, and mortality of the mice were monitored daily. Tumor volume was estimated by using the formula length×width(2)×π/6. Unless otherwise indicated, treatment groups each consisted of five mice. PHY906 (batches number 6, 10, 11 and F which is commercial Huang Qin Tang) were given orally (p.o.) for four days (twice per day (b.i.d), 500 mg/kg) at approximately 10:00 am and 3:00 pm), while CPT-11 (360 mg/kg) was administered intraperitoneally (i.p.) on Day 1. On Day 1, PHY906 was given 30 minutes prior to CPT-11 administration. In the control groups, mice were administered a vehicle, either PBS for i.p. administration or water for oral administration. Data were analyzed by two-way ANOVA (GraphPad Prism 6), The difference was considered to be statistically significant when ++($P<0.001$), +($P<0.05$) and −($P>0.05$).

LC-MS Analysis for Chemical Profiles of the Metabolites of PHY906

The LC-MS analysis was performed on an Agilent 1200 series HPLC coupled with AB SCIEX 4000 QTRAP mass spectrometer. The separation was conducted on an Alltima™ HP HPLC Column (5 mm, 4.6×250 mm). The mobile phase was acetonitrile (A) and water with 0.1% formic acid (B) with gradient elution: 0 min, 5% A; 10 min, 20% A; 20 min, 25% A; 40 min, 30% A; 45 min, 35% A; 55 min, 45% A; 60 min, 70% A; 62 min, 90% A; 67 min, 90% A; 68 min, 5% A; and 75 min, 5% A. The flow rate was 1.0 mL/min, and the column temperature was set at 30° C. ESI negative mode mass spectrometry of scan rate 4000 amu/s was performed with the following ionization parameters: CAD: High; TEM: 550.00° C.; GS1: 55.00; GS2: 50.00; ihe: ON; IS: −4250.00; DP: −40.00; CES 0.00; CE: −5.00. The mass range for detection was 120-800 amu. Using a custom program integrated with MZmine software, the peaks were compared and a clustering analysis was created Algorithm for Determining Correlation Coefficients Graphpad Prism 6 software was used to determine the correlation coefficients. Each raw "if input" table represent different genes or different signal pathways. Each column represents different batches. Values of gene expression or IC50 or AC50 were input. "Column analyses" function of the software was selected for correlation analysis. Correlation between each pairs of column was performed, assuming a sample pool with Gaussian distribution. Pearson coefficients were also calculated.

Cluster analysis was done by using Minitab 17 software. Each raw "if input" table represents different genes or different signal pathways. Each column represents different batches. Values of gene expression or IC50 or AC50 were input. Cluster variable function was selected. Complete linkage method and distance measure-correlation were selected for clustering analysis.

STAR Platform

Luciferase report cell lines for different signaling pathways as listed as the following table.

TABLE 1

| Cell line | Response element DNA sequence | Cell line/ transfection of receptor | Promoter/pathway |
|---|---|---|---|
| CRE | SEQ ID NO: 1 agcctgacgtcagagag x4 | HEK293 | cAMP/PKA |
| NFkB | SEQ ID NO: 2 gggaatttcc x4 | HEK293/HepG2 | NFkB |
| TLR2 | SEQ ID NO: 3 gggaatttcc x4 | TLR2/HEK293 | TLR2 |
| TLR4 | SEQ ID NO: 4 gggaatttcc x4 | TLR4/HEK293 | TLR4 |

TABLE 1-continued

| | | | |
|---|---|---|---|
| GAS (INF γ) | SEQ ID NO: 5 atattactctaaatc x6 | Interferon γ/ HEK293 | STAT1/STAT2 |
| IFN-α/β | SEQ ID NO: 6 tagtttcactttccc x5 | IFN-α/β/HEK293 | STAT1/STAT2 |
| STAT3 | SEQ ID NO: 7 tgcattcccgtaa x6 | HEK293/HEPG2 | STAT3 |
| Lefx12 | SEQ ID NO: 8 agatcaaaggggta x12 | HEK293 | Wnt3a |
| TGFbx4 | SEQ ID NO: 9 gagtatgtctagact x4 | HEK293/HepG2 | TGFb |
| AR | PSA promoter | 22RV1 | Androgen |
| ER-a | SEQ ID NO: 10 ggtcacagtgaccta x4 | ER-a/HEK293 | Estrogen |
| ER-b | SEQ ID NO: 11 ggtcacagtgaccta x4 | ER-b/HEK293 | Estrogen |
| VDR | SEQ ID NO: 12 gatccacaaggttcacgaggttca x3 | Hela | Vitamin D receptor |
| PRE | SEQ ID NO: 13 gggacatggtgttct x4 | T47D | progesterone |
| MR | SEQ ID NO: 14 ggtacattttgttct x4 (same as GRE) | MR/HEK293 | mineralocorticoid |
| NRF2 | SEQ ID NO: 15 tcacagtgactcagcaaaatt x4 | HEK293/HepG2 | Antioxidant Response |

| Cell line | Ligand | Transcriptional factor(s) | Related Function |
|---|---|---|---|
| CRE | forskolin | CREBP | Cell growth |
| NFkB | TNF-a | NF-kB | inflammation |
| TLR2 | PGN | NF-kB | innate immunity |
| TLR4 | LPS | NF-kB | innate immunity |
| GAS (INF γ) | INF γ | STAT1/STAT2 | inflammation |
| IFN-α/β | IFNα | STAT1/STAT2 | inflammation |
| STAT3 | IL6 | Stat3 | inflammation |
| Lefx12 | Wnt3a | b-catenin | Stem cell growth |
| TGFbx4 | TGFb | Smad2/3 | Wound healing/ Differentiation |
| AR | DHT | AR | Prostate cell growth |
| ER-a | E2 Estradiol | ER-a | Endocrine/ hormone |
| ER-b | E2 Estradiol | ER-b | Endocrine/ hormone |
| VDR | Vitamin D3 | Vitamin D receptor | Endocrine/ hormone |
| PRE | progesterone | progesterone receptor | Endocrine/ hormone |
| MR | Aldosterone | mineralocorticoid receptor | Endocrine/ hormone |
| NRF2 | andrographolide | NRF2 | Endocrine/ hormone |

Cells were seeded into haft-area 96-well microplate at 20000 cells/well in 40 µl medium for overnight at 37° C. 5% $CO_2$ incubator. Different doses of PHY906 water extract from 750 µg/ml to 83 µg/ml was added to the cells and placed in 37° C. 5% $CO_2$ incubator. After removing medium at 6 hour, 10 µl of lysis buffer (Tris-HCl 25 mM at pH 7.8, DTT 2 mM, CDTA 2 mM, glycerol 10%, Triton X-100 1%) will be used to lyse the cells and 40 µl of luciferase reaction buffer (Tris-HCl 20 mM at pH 7.8, $NaHCO_3$ 1 mM, $MgSO_4$ 2.5 mM, DTT 10 mM, Coenyzme-A lithium 60 µM, potassium luciferin 225 µM, ATP 250µ was added for reading luminescence using a luminescence microplate reader. IC50 (concentration required to inhibit 50% of control) or EC50 (concentration required to achieved 50% of maximum activation) was determined based on the dose-response curve.

Cox-2 Activity Assay

Cox-2 (Cayman Chemical) enzymatic reactions were performed according to manufacturer's instructions. A four-fold volume of acetonitrile-methanol (2:1) was used to terminate the reaction. After centrifugation, the prostanoid product of the supernatant was quantified by LC-MS. Chromatographic separation was performed using a ZORBAX SB-C18 column (100×2.1 mm, Agilent) at 30° C. The mobile phase consisted of linear gradients of 0.05% (v/v) formic acid (A) and methanol (B): 0.01-5.0 min, 60-60% B (v/v); 5.0-5.5 minutes, 60-80% B; 5.5-35 minutes, 80-80% B; 35-35.5 minutes, 80-60% B; 35.5-40 minutes, 60-60% B. The mobile phase flow rate was 0.3 mL/min. All mass spectrometric experiments were performed on an API 4000 Q-Traq mass spectrometer. The orthogonal Turbo-V source's injectors were heated to 550° C. to allow connection to the HPLC without mobile-phase splitting. Ultrahigh-purity nitrogen ($N_2$) was used as the ion source gas (GS1, GS2), curtain gas (CUR) and collision gas (CAD) and their flow rates were 55, 50, 35, and high, respectively. The multiple reaction monitoring (MRM) experiments in the negative ionization were performed to detect ion transitions at m/z: 303→259, 351.1→315 for arachidonic acid and PGE2 respectively. The collision energies were set at −20, −26V for arachidonic acid and PGE2 respectively. The analyst 1.4.2 software controlled the data acquisition.

iNOS Activity Assay iNOS activity was measured by a colorimetric nitrite assay. One unit iNOS enzyme (Cayman Chemical) was used in a 50 µl reaction consisted of 2 mM $MgAc_2$, 0.2 mM NADPH, 64 µM tetrahydro-L-biopterin, 1 mg/ml BSA, 40 µM DTT, 3 µM $HbO_2$ mix in 0.1M 4-(2-hydroxyethyl)-1-piperazineethanesulfonic acid (HEPES) at pH 7.3. 100 µl L-arginine with or without herbal extract was then added, and the mix was incubated for two hours at 37° C. Next, 100 µl Griess reagent (1% sulfanilamide, 0.1% N-(1-Naphthyl)-ethylenediamine dihydro, and 10% HCl) was added, and the optical density was measured at 540 nm.

gRT-PCR Methods $2 \times 10^5$ HepG2 cell were contacted with PHY906 (batches number 6, 10, 11 and F which is commercial Huang Qin Tang) and seeded in 12 well tissue culture plates in RPMI1640 medium with 5% fatal bovine serum overnight at 37° C. 5% $CO_2$ incubation. HepG2 cell were then treated with water extract of PHY906-6, PHY906-10, PHY906-11, F at final concentration at 850 µg/ml or water as control at 37° C. 5% $CO_2$ incubation for 24 hour. mRNA from HepG2 cells were extracted using a High Pure RNA Isolation Kit from Roche. cDNA was synthesized using random primers and reverse transcriptase MMLV (New England Biolabs, Ipswich, Mass.). qPCR assays were performed using iTaq™ SYBR® Green Supermix and the CFX96 Real-Time PCR Detection System (Bio-Rad Laboratories, Hercules, Calif.). Actin was used as internal control. Primer sets were listed in Table 2.

TABLE 2

| Gene | Forward primer | Reverse primer |
| --- | --- | --- |
| ICAM | SEQ ID NO: 16<br>TATGGCAACGACTCCTTC | SEQ ID NO: 17<br>CATTCAGCGTCACCTTGG |
| IRF5 | SEQ ID NO: 18<br>ATGCTGCCTCTGACCGACCTGGAGA | SEQ ID NO: 19<br>CTTGCTCCAGGCTTATGGGGCCGAA |
| AKR1C1 | SEQ ID NO: 20<br>CCAGAGCACTATAGGCAACCA | SEQ ID NO: 21<br>AACAAGCCAGGGCTCAAGTA |
| HO1 | SEQ ID NO: 22<br>TCCTGCTCAACATCCAGCTCTTTG | SEQ ID NO: 23<br>GGGCAGAATCTTGCACTTTGTTG |
| GCLC | SEQ ID NO: 24<br>CTTTCTCCCCAGACAGGACC | SEQ ID NO: 25<br>CAAGGACGTTCTCAAGTGGG |
| GCLM | SEQ ID NO: 26<br>GTATCAGTGGGCACAGGTAAAAC | SEQ ID NO: 27<br>CTTGCTTCAGAAAGCAGTTCTT |
| Axin2 | SEQ ID NO: 28<br>CTGGCTCCAGAAGATCACAAAG | SEQ ID NO: 29<br>ATCTCCTCAAACACCGCTCCA |
| GDF15 | SEQ ID NO: 30<br>CTCCGAAGACTCCAGATTCCGAGAG | SEQ ID NO: 31<br>CAGCCGCACTTCTGGCGTGAGTAT |
| IGFBP3 | SEQ ID NO: 32<br>CCAGCGCCGCCAGCTCCAGGAAATG | SEQ ID NO: 33<br>CCTTTCTTGATGATGATTATCTTTG |
| OKL38 | SEQ ID NO: 34<br>CTCCCGGTCATCATTGTGGGTAAC | SEQ ID NO: 35<br>GGTAGTCCAGGTCCTGGTCCAG |
| PIM1 | SEQ ID NO: 36<br>CACCAAGCTGGCGCCCGGCAAGGAG | SEQ ID NO: 37<br>ACGTGTTTGATGGCCACCGGCAAG |

TABLE 2-continued

| Gene | Forward primer | Reverse primer |
|---|---|---|
| SERTAD | SEQ ID NO: 38<br>GGAGGAGAAGGAACCTCTGGCAGTC | SEQ ID NO: 39<br>ACTCTGCTGCAGGCTGTGGTGGAGC |
| SOS1 | SEQ ID NO: 40<br>TACTTTGAACTTTTGAAGCAGTTAG | SEQ ID NO: 41<br>AACCGACATGCAGATTCACTCAGTC |
| CPT1A | SEQ ID NO: 42<br>CCACCAAGATCTGGATGGGTATG | SEQ ID NO: 43<br>CACCGACTGTAGATACCTGTTCAC |
| SLC7A11 | SEQ ID NO: 44<br>GTGGGGTCCTGTCACTATTTGGAGC | SEQ ID NO: 45<br>AGCAGTAGCTGCAGGGCGTATTATG |
| BHMT2 | SEQ ID NO: 46<br>CTTTGGACTGGAGTCCAGAGTTG | SEQ ID NO: 47<br>ATACTCCCTTCGAGCCCTTGCTC |
| CD24 | SEQ ID NO: 48<br>ACTGCTCCTACCCACGCAGATTT | SEQ ID NO: 49<br>CACGAAGAGACTGGCTGTTGAC |
| EMP2 | SEQ ID NO: 50<br>GTTCATTGCCACCGTCGACAATGCCTG | SEQ ID NO: 51<br>GCAGCGTGGAGTACTCTTGAAAGCT |
| KRT23 | SEQ ID NO: 52<br>CTGCAGACACAGTACAGCACGAAATC | SEQ ID NO: 53<br>CTTTGATTCTTCCCGTGTCCCTTCAC |
| Actin | SEQ ID NO: 54<br>GCCACGGCTGCTTCCAGCTCC | SEQ ID NO: 55<br>TTGTGCTGGGTGCCAGGGCAGTGA |

Example 1: Correlation of Chemical Analysis and In Vivo Activity

Standard operating protocols of chemical detection were tested for their accuracy in predicting the in vivo efficacy of different batches of herbal compositions. The in vivo activity of different batches of PHY 906 and F (a commercial Huang Qin Tang extract mixture) were tested by co-administering the herbal composition with CPT11 to BDF1 mouse bearing colon 38 tumors. The anti-tumor activity of the HQT/CPT11 treatment was determined, as was the effect of the treatment on the body weight of the subjects. It was found that three of the HQT compositions, PHY906-6, PHY906-10 and PHY906-11, produced using the PHY906 formulation, shared similar anti-tumor and weight loss prevention activity but the fourth HQT composition, a commercial batch of HQT, F, was found to have lower anti-tumor activity and did not prevent weight loss in the subjects (FIG. 1A).

Figure 1D:
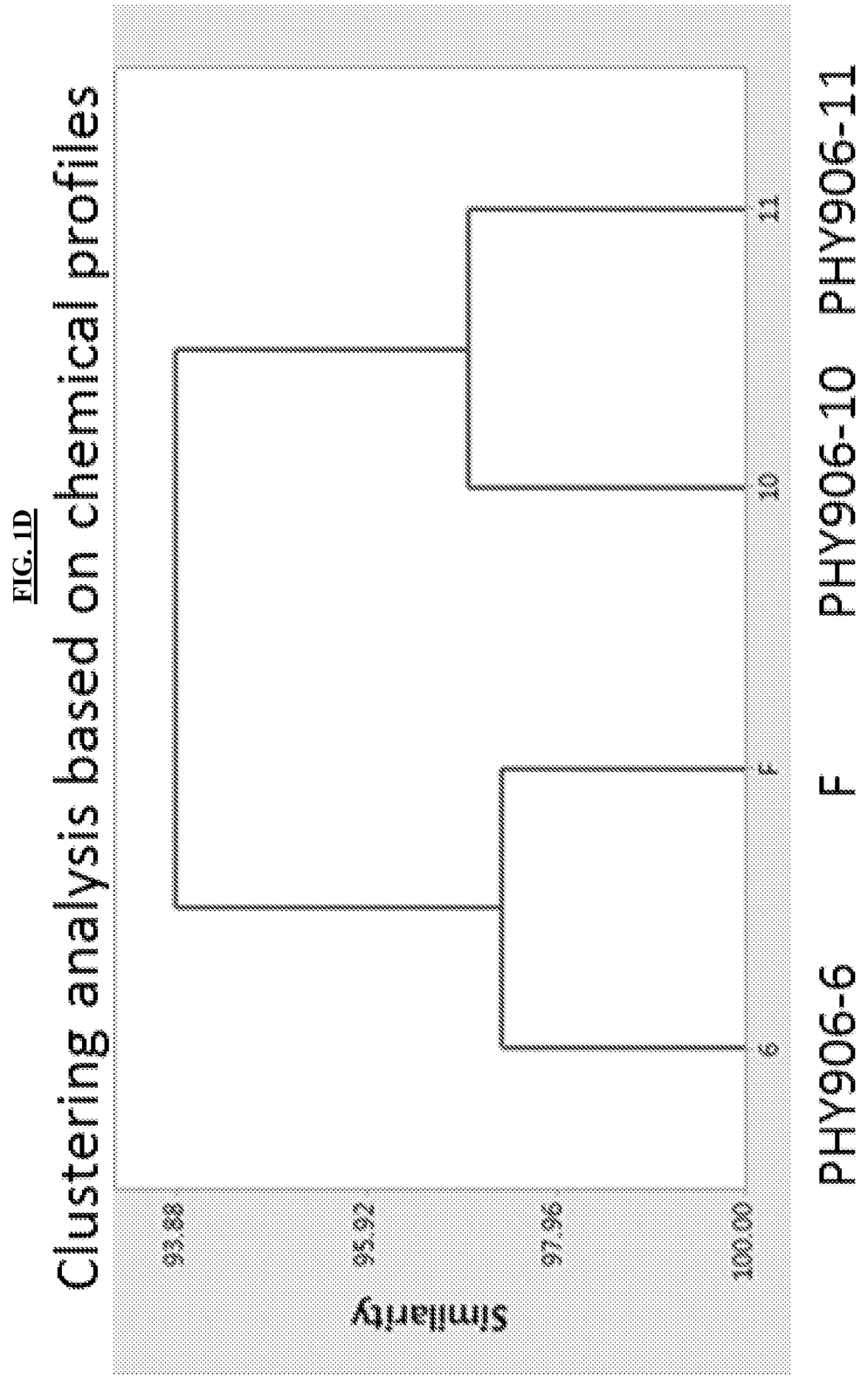

The four batches of HQT were then analyzed by LC-MS according to WHO guidelines to determine the chemical profile of each composition. 73 characteristic peaks were assigned in the LC-MS spectra and then used for similarity analysis (FIG. 1B). Using a custom program integrated with MZmine software, the peaks were compared and a clustering analysis was created (FIGS. 1C-1D). The results of the LC-MS analysis indicated that all four batches of HQT shared similar chemical profiles but that batches PHY906-10 and PHY906-11 were more similar to each other than they were to batches PHY906-6 or F and that batches PHY906-6 and F were more similar to each other than they were to batches PHY906-10 or PHY906-11. This result is in direct contrast to the in vivo results where it would be expected that PHY906-6, PHY906-10 and PHY906-11 would all share very similar chemical profiles and that F would be an outlier.

Example 2: Signal Transduction Activity Response Assays

Figure 2A:
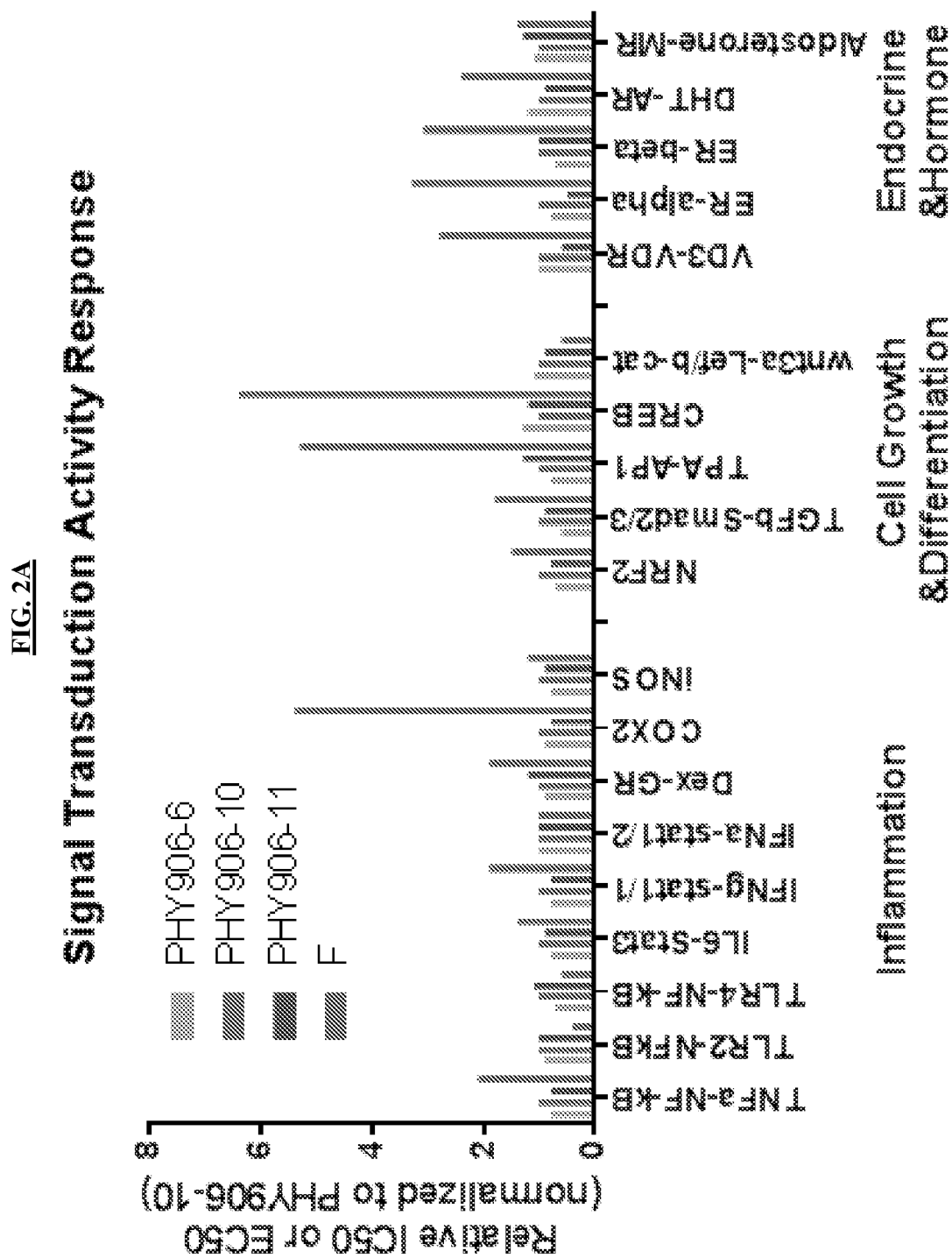
Figure 2C:
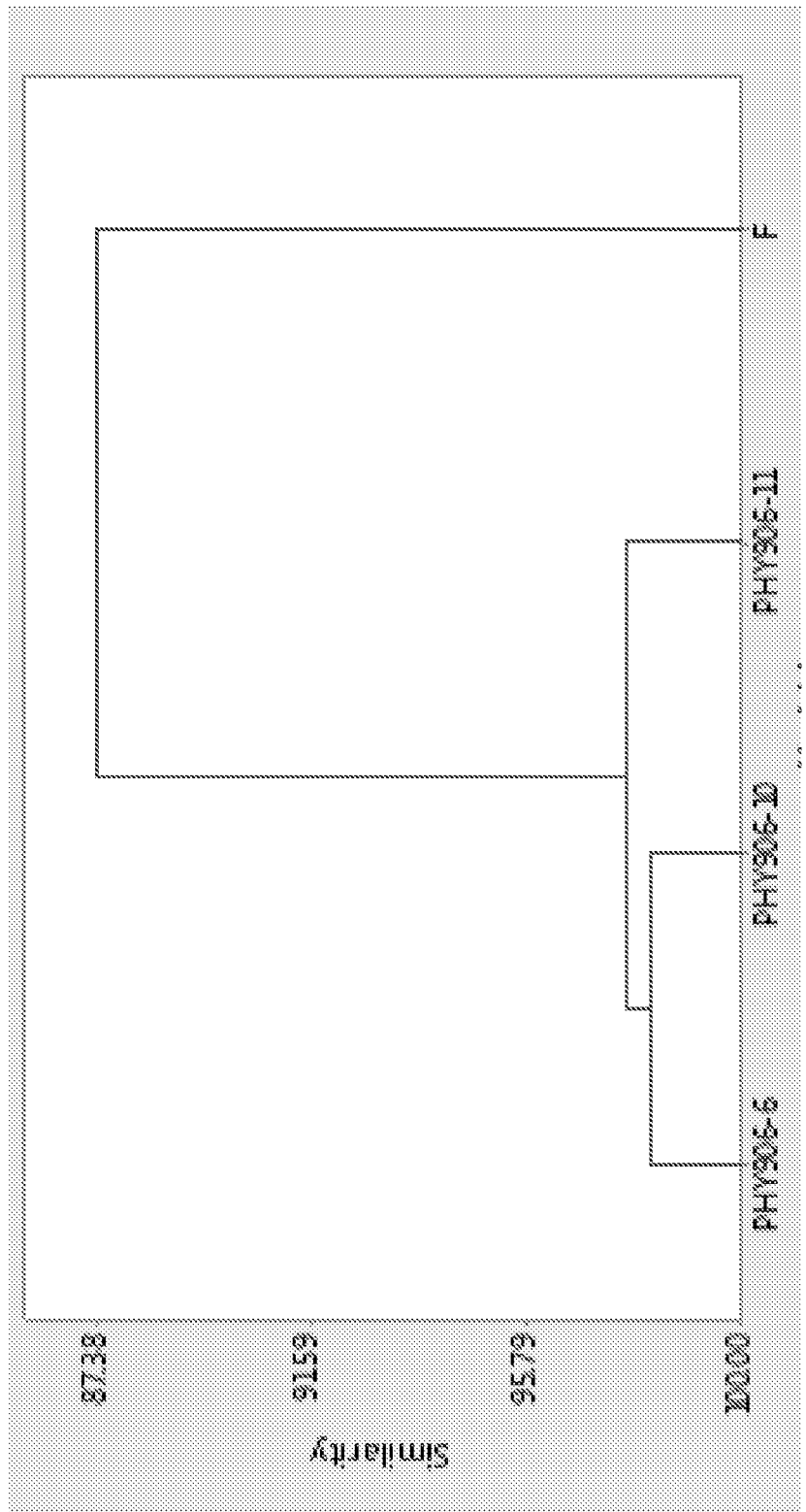

In order to find a more accurate method of determining the quality and potential in vivo activity of a batch of an herbal composition, the four batches of HQT (F, PHY906-6, PHY906-10 and PHY906-11) were screened in a signaling transduction activity response (STAR) platform (FIG. 2A). The STAR platform included 17 mechanism related luciferase reporter cell lines and 2 enzymatic assays relevant to the action of HQT in vivo, including TNFa-NFkB, TLR2-NFkB, TLR4-NFkB, IL6-stat3, IFNg-stat1/1, IFNa-stat1/2, DEX-GR, COX-2, iNOS, NRF2, TGFb-Smad2/3, TPA-AP1, CREB, wnt3a-Lef/b-cat, VD3-VDR, ER-alpha, ER-beta, DHT-AR and aldosterone-MR. It was found that the three batches of PHY906 demonstrated similar IC50 values in the luciferase reporter cell lines and enzymatic assays while the F batch did not (FIGS. 2B-2C). Correlation analysis results based on the results of the STAR platform assays indicated that the PHY906 batches shared a 0.95 correlation coefficient or higher with each other while the F batch demonstrated lower correlation coefficient values. These results indicate that the results of the biological assays of the STAR platform are a better predictor of the potential in vivo activity of a batch of an HQT herbal composition than LC-MS chemical analysis.

Example 3: Gene Expression Analysis

Figure 3C:
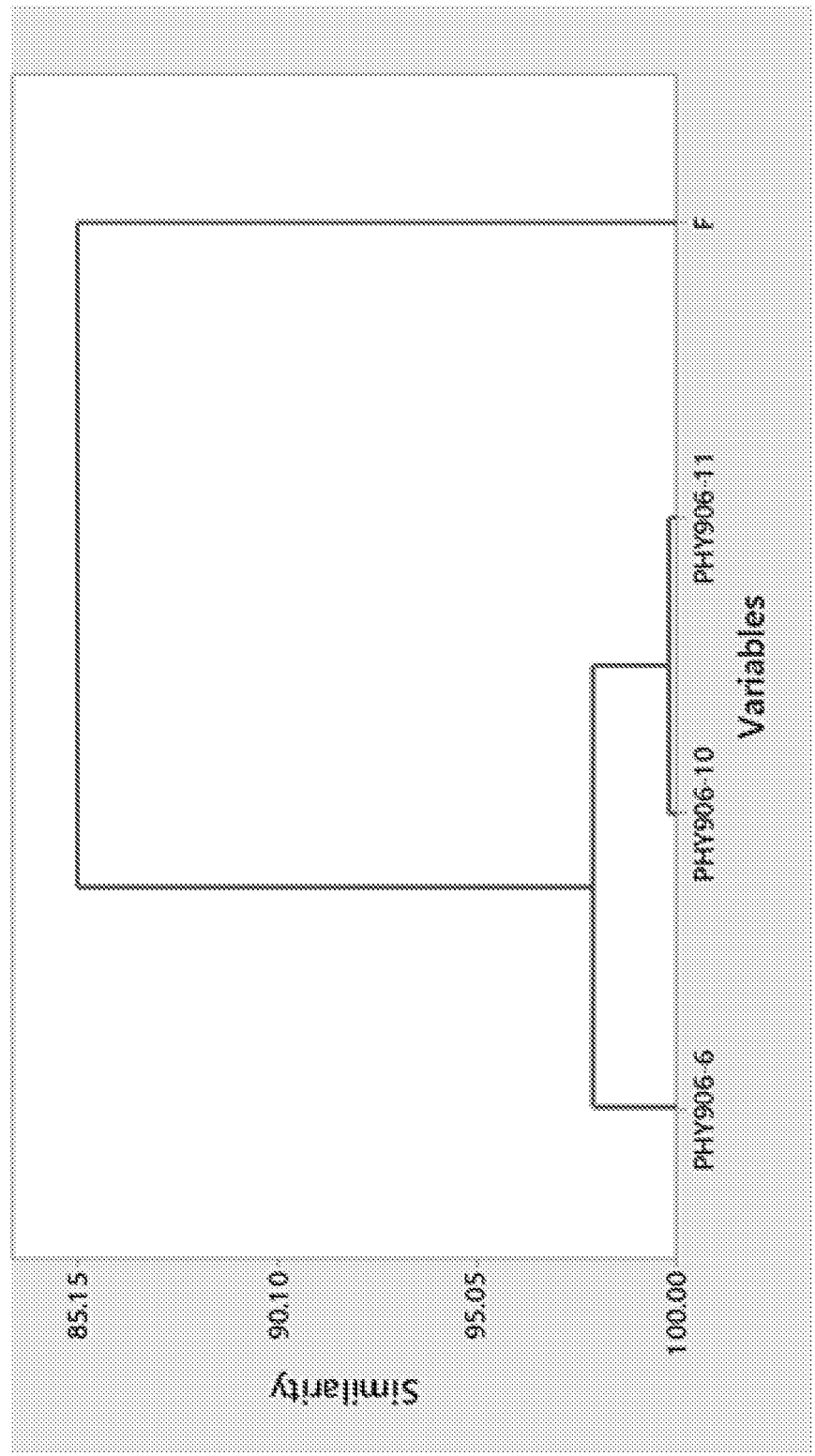

The four batches of HQT were further analyzed using gene expression analysis. The HQT batches were tested against a panel of genes related to previous in vivo DNA array data as well as gene's related to PHY906's hypothesized mechanism of action, including ICAM, IRF5, AKR1C1, HO1, GCLC, GCLM, Axin2, GDF15, IGFBP3, OKL38, PIM1, SERTAD, SOS1, BHMT2, CPT1A, SLC7A11, CD24, EMP2 and KRT23. HepG2 liver cancer cells were treated with a batch of one of the HQT formulations for 24 hours. The mRNA generated was then extracted and analyzed by qRT-PCR (FIG. 3A). It was found that PHY906-6, PHY906-10 and PHY906-11 shared very similar activity in the gene expression panel while F was, again, an outlier (FIG. 3B-3C). These results indicate that gene expression analysis is a better predictor of the potential in vivo activity of a batch of an HQT herbal composition than LC-MS chemical analysis.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of evaluating the quality and potential in vivo activity of a test batch of an herbal composition, the method consisting essentially of subjecting the test batch of the herbal composition to one or more biological analysis methods including:

(a) a signaling transduction activity response assay that comprises measuring the signal transduction activity response against one or more signaling pathways selected from the group consisting of: Tumor necrosis factor alpha-Nuclear factor kappa-light-chain-enhancer of activated B cells (TNFa-NFkB), Toll like receptor 2-Nuclear factor kappa-light-chain-enhancer of activated B cells (TLR2-NFkB), Toll like receptor 4-Nuclear factor kappa-light-chain-enhancer of activated B cells (TLR4-NFkB), Interleukin 6-Signal transducer and activator of transcription 3 (IL6-stat3), Interferon gamma-Signal transducer and activator of transcription 1/1(IFNg-stat1/1), Interferon alpha-Signal transducer and activator of transcription 1/1(IFNa-stat1/2), Dexamethasone-Glucocorticoid receptor (DEX-GR), Cyclooxygenase-2 (COX-2), Inducible nitric oxide synthase (iNOS), Nuclear factor-erythroid factor 2-related factor 2(NRF2), Transforming growth factor beta-Mothers against decapentaplegic homolog 3(TGFb-Smad2/3), Tissue plasminogen activator-Activator protein 1(TPA-AP1), cAMP response element-binding protein (CREB), Wingless/Integrated 3a-Lymphoid enhancer factor/beta catenin (wnt3a-Lef/b-cat), Vitamin D3-vitamin D receptor (VD3-VDR), Estrogen receptors alpha (ER-alpha), Estrogen receptors beta (ER-beta), Dihydrotestosterone-Androgen receptor (DHT-AR), and Aldosterone-Mineralocorticoid receptor (aldosterone-MR); and (b) a gene expression assay, wherein the gene expression assay comprises measurement of one or more protein-encoding genes selected from the group consisting of Intercellular adhesion molecule(ICAM), Interferon regulatory factor 5(IRF5), Aldo-keto reductase family 1 member C1(AKR1C1), heme oxygenase 1 (HO1), Glutamate—cysteine ligase catalytic subunit (GCLC), Glutamate-cysteine ligase modifier Subunit (GCLM), axis inhibition protein 2 (Axin2), Growth/differentiation factor-15(GDF15), Insulin like growth factor binding protein 3(IGFBP3), oxidative stress induced growth inhibitor 1 (OKL38), Pim-1 proto-oncogene, serine/threonine kinase SEI-1, RBT-1, and TARA domain (SERTAD), SOS Ras/Rac guanine nucleotide exchange factor 1 (SOS1), betaine-homocysteine S-methyltransferase 2 (BHMT2), carnitine palmitoyltransferase 1A (CPT1A), solute carrier family 7 member 11(SLC7A11), cluster of differentiation 24 (CD24), Epithelial Membrane Protein 2 (EMP2), and Keratin 23 (KRT23);

and then comparing the test batch results of the biological analysis method with results derived from a known batch of an herbal composition which has a known level of in vivo activity;

wherein if the test batch results have a correlation coefficient of between 0.90 and 1.0 with the known batch results, then the test batch is determined to have sufficiently similar quality as the known batch and potential in vivo activity, and wherein the herbal composition comprises one or more compositions selected from the group consisting of herbal extracts of *Scutellaria baicalensis* (S), *Glycyrrhiza uralensis* (G), *Paeonia lactiflora* (P), *Ziziphus jujuba* (Z), and any fractions thereof.

2. The method of claim 1, wherein the herbal composition is PHY906, wherein PHY906 comprises herbal extracts of *Scutellaria baicalensis* (S), *Glycyrrhiza uralensis* (G), *Paeonia lactiflora* (P), and *Ziziphus jujuba* (Z) in a 3:2:2:2 (S G:P:Z) ratio.

3. The method of claim 1, wherein the signal transduction activity response assay comprises one or more assays selected from the group consisting of luciferase reporter assays and enzymatic assays.

4. The method of claim 1, wherein the gene expression assay comprises: treating hepatoma G2 (HepG2) cells with the herbal composition for 24 h, extracting the messenger ribonucleic acid (mRNA) produced and quantifying the mRNA through real-time quantitative reverse transcription-polymerase chain reaction (qRT-PCR) analysis.

5. The method of claim 1, wherein the one or more biological analysis methods differentiate between active batches of the herbal composition and inactive batches of the herbal composition better than chemical composition analysis methods.

6. The method of claim 5, wherein the chemical composition analysis methods include LC-MS (liquid chromatography—mass spectrometry).

7. The method of claim 1, wherein if the test batch results have a correlation coefficient of between 0.95 and 1.0 with the known batch results, then the test batch is determined to have sufficiently similar quality as the known batch and potential in vivo activity.

8. A method of evaluating the quality and potential in vivo activity of a test batch of an herbal composition, the method consisting essentially of subjecting the test batch of the herbal composition to one or more biological analysis methods including:

(a) a signaling transduction activity response assay that comprises measuring the signal transduction activity response against one or more signaling pathways selected from the group consisting of: Tumor necrosis factor alpha-Nuclear factor kappa-light-chain-enhancer of activated B cells (TNFa-NFkB), Toll like receptor 2-Nuclear factor kappa-light-chain-enhancer of activated B cells (TLR2-NFkB), Toll like receptor 4-Nuclear factor kappa-light-chain-enhancer of activated B cells (TLR4-NFkB), Interleukin 6-Signal transducer and activator of transcription 3 (IL6-stat3), Interferon gamma-Signal transducer and activator of transcription 1/1(IFNg-stat1/1), Interferon alpha-Signal transducer and activator of transcription 1/1(IFNa-stat1/2), Dexamethasone-Glucocorticoid receptor (DEX-GR), Cyclooxygenase-2 (COX-2), Inducible nitric oxide synthase (iNOS), Nuclear factor-erythroid factor 2-related factor 2(NRF2), Transforming growth factor beta-Mothers against decapentaplegic homolog 3(TGFb-Smad2/3), Tissue plasminogen activator-Activator protein 1(TPA-AP1), cAMP response element-binding protein (CREB), Wingless/Integrated 3a-Lymphoid enhancer factor/beta catenin (wnt3a-Lef/b-cat), Vitamin D3-vitamin D receptor (VD3-VDR), Estrogen receptors alpha (ER-alpha), Estrogen receptors beta (ER-beta), Dihydrotestosterone-Androgen receptor (DHT-AR), and Aldosterone-Mineralocorticoid receptor (aldosterone-MR); and (b) a gene expression assay, wherein the gene expression assay comprises measurement of one or more protein-encoding genes selected from the group consisting of Intercellular adhesion molecule(ICAM), Interferon regulatory factor 5(IRF5), Aldo-keto reductase family 1 member C1(AKR1C1), heme oxygenase 1 (HO1), Glutamate-cysteine ligase modifier Subunit (GCLM), axis inhibition protein 2 (Axin2), oxidative stress induced growth inhibitor 1 (OKL38), betaine-homocysteine S-methyltransferase 2 (BHMT2), carnitine palmitoyltransferase 1A (CPT1A), cluster of differentiation 24 (CD24), and Keratin 23 (KRT23);

and then comparing the test batch results of the biological analysis method with results derived from a known batch of an herbal composition which has a known level of in vivo activity;

wherein if the test batch results have a correlation coefficient of between 0.90 and 1.0 with the known batch results, then the test batch is determined to have sufficiently similar quality as the known batch and potential in vivo activity, and wherein the herbal composition comprises one or more compositions selected from the group consisting of herbal extracts of *Scutellaria baicalensis* (S), *Glycyrrhiza uralensis* (G), *Paeonia lactiflora* (P), *Ziziphus jujuba* (Z), and any fractions thereof.

* * * * *